United States Patent [19]
Steinke et al.

[11] Patent Number: 5,240,172
[45] Date of Patent: Aug. 31, 1993

[54] SOLDER ALLOY FOR DENTAL AND JEWELRY PARTS

[75] Inventors: Rudi Steinke, Hanau; Stefan Schittny, Alzenau-Kaelberau; Bernd Kempf, Freigericht; Werner Groll, Alzenau-Hoerstein, all of Fed. Rep. of Germany

[73] Assignee: Degussa Aktiengesellschaft, Hanau, Fed. Rep. of Germany

[21] Appl. No.: 908,785

[22] Filed: Jul. 6, 1992

Related U.S. Application Data

[62] Division of Ser. No. 602,963, Oct. 25, 1990, abandoned.

[30] Foreign Application Priority Data

Oct. 27, 1989 [DE] Fed. Rep. of Germany ....... 3935813

[51] Int. Cl.$^5$ ............................................. B23K 35/30
[52] U.S. Cl. ............................... 228/262.61; 420/508; 420/580; 420/589; 420/587
[58] Field of Search ...................... 228/263.11, 263.18; 420/508, 580, 587, 589

[56] References Cited

U.S. PATENT DOCUMENTS 4,473,621 9/1984 Drylie ..................... 228/263.18 X

FOREIGN PATENT DOCUMENTS

| | | |
|---|---|---|
| 0234790 | 9/1987 | European Pat. Off. . |
| 2828304 | 2/1979 | Fed. Rep. of Germany . |
| 63-024050 | 2/1988 | Japan . |
| 683004 | 11/1952 | United Kingdom . |

*Primary Examiner*—Kenneth J. Ramsey
*Attorney, Agent, or Firm*—Beveridge, DeGrandi, Weilacher & Young

[57] ABSTRACT

White solder alloys for dental and jewelry parts, with working temperatures around 1000° C., contain 38 to 70% by weight gold, 6 to 20% by weight palladium, 8 to 40% by weight silver, 1 to 6% by weight iron and/or cobalt, 0 to 10% by weight copper, 0–5% each by weight indium, zinc and tin, 0 to 4% each by weight gallium and germanium, ruthenium and/or rhenium. The sum of the contents of tin, zinc, indium, gallium and germanium can be between 1 and 5% by weight.

5 Claims, No Drawings

SOLDER ALLOY FOR DENTAL AND JEWELRY PARTS

This application is a division of application Ser. No. 07/602,963, filed Oct. 25, 1990, now abandoned.

INTRODUCTION TO THE INVENTION

The present invention relates to a solder alloy for dental and jewelry parts, and which is based on gold-palladium-silver with additional base metal components.

The cost reduction measures in the health system in the Federal Republic of Germany have resulted in recent years in an increased use of gold-reduced palladium-based alloys in dentistry. In contrast to many alloys with a high gold content, these alloys exhibit a white color. The solders previously used in dentistry are often not optimally adapted to these new alloys in regards to the color since they usually have a yellow or yellowish color.

Nickel is frequently used as a whitener of gold alloys. However, it is known that nickel-containing alloys can cause allergies in humans. Nickel should therefore be avoided if possible in dentistry. The same applies to other toxic elements such as e.g. cadmium, which is frequently added to solders to lower the melting range. A corresponding solder is described in Germa patent 732,318.

Dental solder alloys must meet a number of requirements. They must be mouth-resistant, exhibit good wetting behavior and flow behavior, and be adapted in their color and working temperature to the alloys to be soldered. The solder connection must exhibit great strength.

In the case of dental parts which are provided with a ceramic veneer, the solder connections must exhibit a sufficient strength even at firing temperatures of 950° to 980° C., so that no dimensional changes occur in soldered parts. Since the production of metallic dentures (dental prostheses) takes place in several stages, it is advantageous to have a so-called second (secondary) solder in addition to a first (primary) solder, where the secondary solder is so much lower in its working temperature that subsequent solderings can be carried out without reloosening the first-soldered connection.

Nickel-containing solders are frequently used for soldering removable partial dentures, which are preferable made with base metal alloys (e.g. cobalt-chromium alloys). In the connection of base metal parts and noble metal parts, the base metal is first presoldered with a nickel-containing solder and thereafter soldered with a lower-melting solder. Since the base metal alloys exhibit a white color, a white solder alloy is also advantageous in this instance. A working temperature of above 1000° C. is also necessary if the base metal denture is veneered with ceramics.

In order to lower the melting range vis-á-vis the dental alloys which are composed in principle in a similar manner, low-melting elements such as zinc, tin, indium, gallium or germanium are alloyed to the solder alloys. Two corresponding alloy types based on gold are described in German Patent 2,638,837 and in U.S. Pat. No. 3,892,564. Both solder types exhibit working temperatures in a range of 590° C. to a maximum of 850° C. They can therefore not be used for parts which are subjected to a ceramic firing.

Solders are also sought in the area of jewelry alloys which coincide in their color as exactly as possible with the parts to be soldered and which yield high strengths of the solder connections. Since toxic and allergenic elements are also avoided to the extent possible in the jewelry sector, it is advantageous if the solder used does not exhibit any corresponding alloy components. It is advantageous in the case of nickel-free white gold in particular to also have a white, nickel-free solder available.

SUMMARY OF THE INVENTION

An object of the present invention was to develop a solder alloy for dental parts (e.g., bridges, crowns, clamps) and jewelry parts (e.g., rings, broaches) based on gold-palladium-silver with additional base metal components which is similar in its color to the white gold-palladium alloys and gold-based alloys in dentistry, is free of components which could be injurious to one's health, and whose high-temperature strength permits solderings prior to the ceramic firing.

In addition, the solder alloy should be able to be used in base metal dental alloys and in jewelry parts.

Other objects include methods for soldering jewelry pieces and for soldering dental parts.

DETAILED DESCRIPTION OF THE INVENTION

According to the present invention this and other objects are achieved by the development of an alloy which contains 38 to 70% by weight gold, 6 to 20% by weight palladium, 8 to 40% by weight silver, 1 to 6% by weight iron and/or cobalt, 0 to 10% by weight copper, 0 to 5% by weight tin, 0 to 5% by weight zinc, 0 to 5% by weight indium, 0 to 4% by weight gallium, 0 to 4% by weight germanium, 0 to 1% by weight tungsten, and 0 to 1% by weight iridium, ruthenium and/or rhenium, and that the sum of the contents of tin, zinc, indium, gallium and germanium may be at least 1% by weight and at the most 5% by weight.

It is preferable to use alloys with 50 to 70% by weight gold, 8 to 20% by weight palladium, 14 to 20% by weight silver, 1 to 6% by weight iron and/or cobalt, 1 to 10 % by weight copper, 0 to 5% by weight tin, 0 to 5% by weight zinc, 0 to 5% by weight indium, 0 to 4% by weight gallium, 0 to 4% by weight germanium, 0 to 1% by weight tungsten, and 0 to 1% by weight iridium, ruthenium and/or rhenium, and that the sum of the contents of tin, zinc, indium, gallium and germanium must be between 1 and 5% by weight.

In the case of dental and jewelry parts with an almost pure white tint, a solder alloy should be used which contains 55 to 70% by weight gold and 12 to 16% by weight palladium in addition to the other components.

The addition of 1 to 6% by weight iron and/or cobalt to gold-silver alloys results in a surprising manner in an elevation of the tensile strength of these alloys at room temperature and at 900° C. Tensile strengths of up to 500 MPa are thereby achieved at room temperature. Moreover, iron and cobalt also exert a favorable influence on the white color of the alloy due to their strong decoloring action. It is possible for this reason to keep the amount of the whitener palladium relatively low since an elevation of the palladium content results in an undesired increase of the working temperature. Therefore, solder alloys with 55 to 70% by weight gold and 12 to 16% by weight palladium are especially suitable for white, procelain fused metal alloys and white base metal alloys since they are very similar in their tint to the white alloys.

The elements zinc, tin, indium, gallium and germanium serve to lower the melting range and to improve the flowability. However, their total amount is limited to approximately 5% in sum since a greater amount results in an embrittlement of the material, which renders the production of the solder in its customary form as a band or a thin rod-shaped material very difficult.

The working temperature can be adjusted to a large extent via the variation of the copper content without adversely influencing the ductility to any great degree. The white color of the solder alloys is thereby influenced almost not at all if the elevation of the copper content is compensated by a lowering of the gold content.

The addition of up to 1% by weight tungsten results in an improved flow behavior and wetting behavior of the liquid solders and in more reliable solder connections. Iridium, ruthenium and rhenium can be alloyed in order to get a fine-grained structure.

The alloys are only suitable for soldering metallic parts. Metal on ceramic can not be soldered. The following alloys are typically soldered: gold alloys (e.g., gold with platinum, palladium and/or silver); palladium alloys (e.g., palladium with gold and/or silver); white gold alloys without nickel; and cobalt-chromium alloys.

EXAMPLES

The melting range, the working temperature and the tensile strength of a few solder alloys in accordance with the invention are indicated in the following tables:

TABLE

| Alloy | Au | Pd | Ag | Others |
|---|---|---|---|---|
| 1 | 66 | 14 | 14 | 2.8 Co 1.4 In 1.4 Zn 0.2 Ir |
| 2 | 59.4 | 14 | 14 | 7.0 Cu 2.9 Fe 2.0 In 0.5 W 0.2 Ir |
| 3 | 58.4 | 8 | 20 | 7.0 Cu 2.0 Fe 3.0 In 1.0 Sn 0.5 W 0.1 Ir |
| 4 | 38.9 | 8 | 40 | 7.0 Cu 2.0 Fe 4.0 In 0.1 Ir--. |

| | Melting range (°C.) | Working temperature (°C.) | Tensile strength at 20° C. | MPa at 900° C. |
|---|---|---|---|---|
| 1 | 1082–1141 | 1120 | 552 | 26 |
| 2 | 995–1075 | 1070 | 522 | 25 |
| 3 | 914–975 | 960 | 598 | not documented |
| 4 | 850–937 | 950 | not documented | |

In carrying out the method of soldering together at least two jewelry pieces, a solder alloy composition comprising 38 to 70% by weight gold, 6 to 20% by weight palladium, 8 to 40% by weight silver, 1 to 6% by weight iron or cobalt or a mixture of the two, 0 to 10% by weight copper, 0 to 5% by weight tin, 0 to 5% by weight zinc, 0 to 5% by weight indium, 0 to 4% by weight gallium, 0 to 4% by weight germanium, 0 to 1% by weight tungsten and 0 to 1% by weight of at least one member selected from the group consisting of iridium, ruthenium and rhenium, wherein the sum of the contents of tin, zinc, indium, gallium and germanium is optionally at least 1% by weight and at most 5% by weight, is heated to a temperature sufficient to reach the working temperature of the solder alloy composition. The solder, heated to a temperature in the working temperature range, is placed in contact with at least a first gold or gold alloy jewelry piece and another gold or gold alloy jewelry piece is soldered to the first piece. More than two jewelry pieces may be soldered together.

The method of soldering together jewelry pieces can further comprise matching the color of the solder to the color of the jewelry pieces as an initial step.

In carrying out the method of soldering together at least two dental parts, a solder alloy composition comprising 38 to 70% by weight gold, 6 to 20% by weight palladium, 8 to 40% by weight silver, 1 to 6% by weight iron or cobalt or a mixture of the two, 0 to 10% by weight copper, 0 to 5% by weight tin, 0 to 5% by weight zinc, 0 to 5% by weight indium, 0 to 4% by weight gallium, 0 to 4% by weight germanium, 0 to 1% by weight tungsten and 0 to 1% by weight of at least one member selected from the group consisting of iridium, ruthenium and rhenium, wherein the sum of the contents of tin, zinc, indium, gallium and germanium is optionally at least 1% by weight and at most 5% by weight, is heated to a temperature sufficient to reach the working temperature of the solder alloy composition. The solder, heated to a temperature in the working temperature range, is placed in contact with at least a first gold or gold alloy dental piece and another gold or gold alloy dental piece is soldered to the first piece. More than two dental pieces may be soldered together.

The solder alloy compositions described above can comprise 50 to 70% by weight gold, 8 to 20% by weight palladium, 14 to 20% by weight silver, 1 to 6% by weight iron or cobalt or a mixture of the two, 1 to 10% by weight copper, 0 to 5% by weight tin, 0 to 5% by weight zinc, 0 to 5% by weight indium, 0 to 4% by weight gallium, 0 to 4% by weight germanium, 0 to 1% by weight tungsten and 0 to 1% by weight of at least one member selected from the group consisting of iridium, ruthenium and rhenium, wherein the sum of the contents of tin, zinc, indium, gallium and germanium is between 1 and 5% by weight.

Parts of a dental bridge made from a gold alloy (38.5% palladium, 9% indium, the balance gold) were soldered together using solder number 1.

Separated bridge sections of a palladium alloy (11.5% Cu, 7.5% gallium, the balance palladium) was soldered with solder number 2.

A ring of white gold (9.5% silver, 10.5% copper, the balance gold) was soldered with solder number 3 into an arrangement using the same gold material.

Further variations and modifications of the invention will become apparent to those skilled in the art from the foregoing and are intended to be encompassed by the claims appended hereto.

What is claimed is:

1. A method of soldering together at least two jewelry pieces, comprising (a) heating a solder alloy composition comprising 38 to 70% by weight gold, 6 to 20% by weight palladium, 8 to 40% by weight silver, 1 to 6% by weight iron or cobalt or a mixture of the two, 0 to 10% by weight copper, 0 to 5% by weight tin, 0 to 5% by weight zinc, 0 to 5% by weight indium, 0 to 4% by weight gallium, 0 to 4% by weight germanium, 0 to 1% by weight tungsten and 0 to 1% by weight of at least one member selected from the group consisting of iridium, ruthenium and rhenium, wherein the sum of the contents of tin, zinc, indium, gallium and germanium is optionally at least 1% by weight and at most 5% by weight, to a temperature sufficient to reach the working temperature of said solder, (b) placing said solder heated to a temperature in the working temperature range in contact with at least a first gold or gold alloy jewelry piece and (c) soldering another gold or gold alloy jewelry piece to said first piece.

2. The method according to claim 1, wherein said solder alloy composition comprises 50 to 70% by weight gold, 8 to 20% by weight palladium, 14 to 20% by weight silver, 1 to 6% by weight iron or cobalt or a mixture of the two, 1 to 10% by weight copper, 0 to 5% by weight tin, 0 to 5% by weight zinc, 0 to 5% by weight indium, 0 to 4% by weight gallium, 0 to 4% by weight germanium, 0 to 1% by weight tungsten and 0 to 1% by weight of at least one member selected from the group consisting of iridium, ruthenium and rhenium, wherein the sum of the contents of tin, zinc, indium, gallium and germanium is between 1 and 5% by weight.

3. The method according to claim 1, further comprising matching the color of said solder to the color of said jewelry pieces as an initial step.

4. A method of soldering together at least two dental parts, comprising (a) heating a solder alloy composition comprising 38 to 70% by weight gold, 6 to 20% by weight palladium, 8 to 40% by weight silver, 1 to 6% by weight iron or cobalt or a mixture of the two, 0 to 10% by weight copper, 0 to 5% by weight tin, 0 to 5% by weight zinc, 0 to 5% by weight indium, 0 to 4% by weight gallium, 0 to 4% by weight germanium, 0 to 1% by weight tungsten and 0 to 1% by weight of at least one member selected from the group consisting of iridium, ruthenium and rhenium, wherein the sum of the contents of tin, zinc, indium, gallium and germanium is optionally at least 1% by weight and at most 5% by weight, to a temperature sufficient to reach the working temperature of said solder, (b) placing said solder heated to a temperature in the working temperature range in contact with at least a first gold or gold alloy dental piece and (c) soldering another gold or gold alloy dental piece to said first piece.

5. The method according to claim 4, wherein said solder alloy composition comprises 50 to 70% by weight gold, 8 to 20% by weight palladium, 14 to 20% by weight silver, 1 to 6% by weight iron or cobalt or a mixture of the two, 1 to 10% by weight copper, 0 to 5% by weight tin, 0 to 5% by weight zinc, 0 to 5% by weight indium, 0 to 4% by weight gallium, 0 to 4% by weight germanium, 0 to 1% by weight tungsten and 0 to 1% by weight of at least one member selected from the group consisting of iridium, ruthenium and rhenium, wherein the sum of the contents of tin, zinc, indium, gallium and germanium is between 1 and 5% by weight.

* * * * *